United States Patent
Kanamoto et al.

(10) Patent No.: US 9,427,563 B2
(45) Date of Patent: Aug. 30, 2016

(54) BLOOD-FLOW-PATH SWITCHING DEVICE AND BLOOD-BAG SYSTEM

(71) Applicant: TERUMO KABUSHIKI KAISHA, Tokyo (JP)

(72) Inventors: Kazuaki Kanamoto, Kanagawa (JP); Kaoru Hosoe, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 197 days.

(21) Appl. No.: 14/383,792

(22) PCT Filed: Feb. 12, 2013

(86) PCT No.: PCT/JP2013/053190
§ 371 (c)(1),
(2) Date: Sep. 8, 2014

(87) PCT Pub. No.: WO2013/136888
PCT Pub. Date: Sep. 19, 2013

(65) Prior Publication Data
US 2015/0133879 A1   May 14, 2015

(30) Foreign Application Priority Data

Mar. 12, 2012 (JP) ................. 2012-054121

(51) Int. Cl.
*A61B 19/00* (2006.01)
*A61M 39/22* (2006.01)
(Continued)

(52) U.S. Cl.
CPC ......... *A61M 39/221* (2013.01); *A61M 1/0218* (2014.02); *A61M 1/0236* (2014.02);
(Continued)

(58) Field of Classification Search
CPC ............... A61M 39/10; A61M 39/18; A61M 2039/221; A61M 2039/222; A61M 2039/1072; A61M 1/0236; A61M 29/26
See application file for complete search history.

(56) References Cited

U.S. PATENT DOCUMENTS 3,127,892 A * 4/1964 Bellamy, Jr. .............. A61J 1/10
  128/DIG. 24
4,878,516 A * 11/1989 Mathieu ................ A61M 39/18
  137/240
(Continued)

FOREIGN PATENT DOCUMENTS

EP    0116986 A1   8/1984
EP    0197553 A2   10/1986
(Continued)

OTHER PUBLICATIONS

International Search report for PCT Application No. PCT/JP2013/053190, issued by the Japanese Patent Office on Apr. 23, 2013.
(Continued)

*Primary Examiner* — Leslie Deak
(74) *Attorney, Agent, or Firm* — John R. Merkling

(57) ABSTRACT

In a blood-flow-path switching device and a blood-bag system, a tube-shaped body (68) includes a body tube (69) extending in an axial direction and a branching tube (71) extending in a direction branching from the axial direction, and a blocking part (74) is provided in a hollow section (69*c*) of the body tube (69). A communicating part (70) movable in the axial direction is provided in the hollow section (69*c*). By moving the communicating part (70) in a pushing direction and creating an opening by penetrating the blocking part (74), a communication of a first port (86) and a third port (90) is blocked, and at the same time, the first port (86) and a second port (88) are communicated with each other.

12 Claims, 6 Drawing Sheets

(51) Int. Cl.
*A61M 1/02* (2006.01)
*A61M 39/26* (2006.01)
A61J 1/10 (2006.01)
A61M 39/10 (2006.01)

(52) U.S. Cl.
CPC ............... *A61M 39/26* (2013.01); *A61J 1/10* (2013.01); *A61M 2039/1072* (2013.01); *A61M 2039/1083* (2013.01); *A61M 2039/1088* (2013.01); *A61M 2039/222* (2013.01)

(56) References Cited

U.S. PATENT DOCUMENTS

| 6,328,726 | B1 | 12/2001 | Ishida et al. |
| 6,482,189 | B2* | 11/2002 | Dopper ............... A61M 1/285 604/284 |
| 6,626,884 | B1 | 9/2003 | Dillon et al. |
| 7,097,209 | B2 | 8/2006 | Unger et al. |
| 8,066,648 | B1 | 11/2011 | Mark |
| 2010/0108681 | A1 | 5/2010 | Jepson et al. |
| 2011/0288441 | A1 | 11/2011 | Taguchi |

FOREIGN PATENT DOCUMENTS

| JP | 3776227 B2 | 5/2006 |
| JP | 2008149066 A | 7/2008 |
| JP | 200945394 A | 3/2009 |
| JP | 201230110 A | 2/2012 |
| WO | WO82/04187 A1 | 12/1982 |
| WO | WO2004/004823 A1 | 1/2004 |

OTHER PUBLICATIONS

Supplemental European Search Report and Search Opinion for EP Application No. 13761140.6, dated May 20, 2015, performed by the European Patent Office, 6 pages, Munich Germany.

* cited by examiner

BLOOD-FLOW-PATH SWITCHING DEVICE AND BLOOD-BAG SYSTEM

TECHNICAL FIELD

The present invention relates to a blood-flow-path switching device used to secure a flow path of blood and a blood-bag system including the blood-flow-path switching device.

BACKGROUND ART

In a blood donation or the like, when drawing blood from a subject by using a blood drawing apparatus, a blood drawing needle is punctured in the subject, and the blood of the subject is drawn from the blood drawing needle and introduced to a blood drawing bag. At this moment, by sanitizing a puncture position of the subject with alcohol or the like before puncturing the blood drawing needle in the subject, the drawn blood is prevented from being contaminated by bacteria. However, even after the sanitization is performed, the drawn blood can be contaminated by bacteria that are present on a skin or under the skin. When the drawn blood is contaminated by bacteria by mistake, depending on types of the bacteria, the bacteria may grow even during a period of storing the blood in the blood drawing bag or in a collecting bag. If such blood that is contaminated by the bacteria is transfused into other patient, it may cause an infectious disease, which is likely to lead to a serious situation.

For this reason, in order to prevent the drawn blood from being contaminated by the bacteria, particularly to remove initially-drawn blood at the time of drawing the blood, a blood drawing apparatus has been proposed, in which a first flow path for introducing drawn blood to a blood drawing bag and a second flow path for removing initially-drawn blood are connected to each other with a branching part, and a blocking part is provided between the branching part and the blood drawing bag, which blocks the flow path at the initial stage but opens the flow path by an opening operation (see, for example, Japanese Patent No. 3776227).

This blocking part is partially breakable. The first flow path is blocked by the blocking part before being broken, so that the initially-drawn blood is prevented from flowing into the blood drawing bag. On the other hand, when the blocking part is partially broken, the first flow path is opened, so that the drawn blood can be introduced to the blood drawing bag.

Another technology uses a multiway valve as a flow-path switching device for switching a flow path of blood between a blood drawing tube connected to a blood drawing bag and an initially-drawn blood introducing tube connected to an initially-drawn blood removing bag (see, for example, JP 2008-149066 A).

SUMMARY OF INVENTION

However, in the blood drawing apparatus described in Japanese Patent No. 3776227, when opening the first flow path, a sold pillar part is separated by breaking a breaking part on the blocking part, and a considerably large force is required for the breaking operation. Therefore, the opening of the front and back flow paths can be hardly performed with ease, i.e., an operator can hardly perform the opening of the flow path in the blood drawing apparatus with an easy operation. Furthermore, the breaking of the breaking part is insufficient in some cases, and in such a case, a flow path enough to smoothly flow the blood cannot be ensured, possibly causing a poor flow of the blood so that the blood is hemolyzed.

Further, in the flow-path switching device described in JP 2008-149066 A, the flow path is switched by rotating a valve member in the multiway valve, and hence the flow of the blood is disrupted during the rotation of the valve member. In addition, a poor flow of the blood is likely to occur at a connection portion of a branching tube to which the blood drawing tube or the initially-drawn blood introducing tube is connected and a flow path in the valve member, possibly causing a hemolysis of the blood.

The present invention has been achieved in view of the above aspects, and it is an object of the present invention to provide a blood-flow-path switching device configured to switch a flow path that branches in multiway with an easy operation and to ensure a sufficient flow path of blood at the switching portion and a blood-bag system including the blood-flow-path switching device.

In order to achieve the above-mentioned object, a blood-flow-path switching device according to the present invention includes a tube-shaped body and a communicating part each having a flow path of a fluid in a hollow section formed in a hollow shape, wherein the tube-shaped body includes a body tube in a hollow shape extending in an axial direction, and a branching tube in a hollow shape connected to a halfway portion of the body tube extending in a direction branching from the axial direction, the hollow section of the body tube includes a blocking part for blocking a flow of the fluid in the hollow section, the blocking part blocks a communication of a first port disposed on one side with respect to the blocking part and a second port disposed on the other side, the branching tube is connected to the body tube on a side of the first port with respect to the blocking part and includes a third port disposed on the side of the first port with respect to the blocking part and communicable with the first port, the communicating part is movable in the axial direction in the hollow section of the body tube and is disposed in a movable manner to a predetermined moving position in a moving direction toward the blocking part, and when the communicating part moves to the predetermined moving position, the communication of the first port and the third port is blocked, the blocking part is opened, and the first port and the second port are communicated with each other.

According to the above-mentioned configuration, the communicating part is movable in the axial direction in the hollow section of the tube body in which the blocking part is provided in the tube-shaped body, and hence by simply pushing the communicating part with respect to the tube-shaped body, the flow path connected to the blood-flow-path switching device can be switched. Further, as the flow path is opened by the movement of the communicating part with respect to the body tube, a flow path of a sufficient size can be secured at a switching portion.

The above-mentioned blood-flow-path switching device may further include a cover part in a hollow shape shrinkable in the axial direction configured to accommodate the communicating part, wherein a distal end part positioned to the front in the moving direction in the cover part may be connected to the body tube in a liquid-tight manner, and a base end part positioned to the rear in the moving direction in the cover part may be connected to the communicating part in a liquid-tight manner and the base end part may be provided to be movable in the axial direction together with the communicating part. This cover part enables the communicating part to be kept clean, and prevents the fluid from leaking outside even if the fluid leaks from the communicating part.

In the above-mentioned blood-flow-path switching device, the communicating part may be disposed on the side of the first port with respect to the blocking part in the tube-shaped body. With this configuration, after the blocking part is opened by the communicating part, blood introduced from the first port is introduced to the second port via a distal end part of the communicating part, and hence a sufficient flow path of the blood can be secured.

In the above-mentioned blood-flow-path switching device, the communicating part may be disposed on a side of the second port with respect to the blocking part in the tube-shaped body. With this configuration, before the blocking part is opened by the communicating part, blood introduced from the first port is introduced as it is to a hollow section of the branching tube and the third port, and hence a sufficient flow path of the blood can be secured.

In the above-mentioned blood-flow-path switching device, the hollow section may define the flow path of the communicating part, wherein a distal end part positioned to the front in the moving direction in the communicating part may constitute the communicating part on a side of the blocking part and may be formed in a shape capable of penetrating the blocking part, and the blocking part may be opened by being penetrated by the communicating part that moves in the moving direction with respect to the body tube. In this manner, due to a configuration of penetrating the blocking part by the communicating part, the switching of the flow path can be performed with ease, and at the same time, an even more sufficient flow path can be secured.

In the above-mentioned blood-flow-path switching device, the cover part may be formed in an accordion shape. By forming the cover part in an accordion shape, the cover part can be easily shrunken in the axial direction, and hence an operating force required for a connection operation of the flow path can be further reduced.

Further, a blood-bag system according to the present invention includes: a bag for accommodating blood or blood component; a tube that defines a flow path of the blood or the blood component to the bag; and a blood-flow-path switching device disposed for the tube, wherein the blood-flow-path switching device includes a tube-shaped body and a communicating part each having a flow path of a fluid in a hollow section formed in a hollow shape, the tube-shaped body includes a body tube in a hollow shape extending in an axial direction, and a branching tube in a hollow shape connected to a halfway portion of the body tube and extending in a direction branching from the axial direction, the hollow section of the body tube includes a blocking part for blocking a flow of the fluid in the hollow section, the blocking part blocks a communication of a first port disposed on one side with respect to the blocking part and a second port disposed on the other side, the branching tube is connected to the body tube on a side of the first port with respect to the blocking part and includes a third port disposed on the side of the first port with respect to the blocking part and communicable with the first port, the communicating part is movable in the axial direction in the hollow section of the body tube and is disposed in a movable manner to a predetermined moving position in a moving direction toward the blocking part, and when the communicating part moves to the predetermined moving position, the communication of the first port and the third port is blocked, the blocking part is opened, and the first port and the second port are communicated with each other.

According to the above-mentioned configuration, by simply pushing the communicating part with respect to the tube-shaped body, the flow path connected to the blood-flow-path switching device can be switched with ease, and hence a flow of the blood in the blood path tube disposed in the blood-bag system can be switched with ease. Further, as the flow path is opened by the movement of the communicating part with respect to the body tube, a flow path of a sufficient size can be secured at a switching portion.

In the above-mentioned blood-bag system, the blood-flow-path switching device may further include a cover part in a hollow shape shrinkable in the axial direction configured to accommodate the communicating part, wherein a distal end part positioned to the front in the moving direction in the cover part may be connected to the body tube in a liquid-tight manner, and a base end part positioned to the rear in the moving direction in the cover part may be connected to the communicating part in a liquid-tight manner, and the base end part may be provided to be movable in the axial direction together with the communicating part. This cover part enables the communicating part to be kept clean, and prevents the fluid from leaking outside even if the fluid leaks from the communicating part.

In the above-mentioned blood-bag system, the communicating part may be disposed on the side of the first port with respect to the blocking part in the tube-shaped body. With this configuration, after the blocking part is opened by the communicating part, blood introduced from the first port is introduced to the second port via a distal end part of the communicating part, and hence a sufficient flow path of the blood can be secured.

In the above-mentioned blood-bag system, the bag may include a blood drawing bag for accommodating the blood drawn from a donor, and an initially-drawn blood bag for drawing initially-drawn blood in a blood drawing, and the tube may include a first blood drawing tube connected to a blood drawing needle to be punctured in the donor and connected to the first port that defines a base end part positioned to the rear in the moving direction in the communicating part, a second blood drawing tube connected to the blood drawing bag and connected to the second port that defines one end part of the body tube, and a branching tube connected to the initially-drawn blood bag and connected to the third port that defines one end part of the branching tube. With this configuration, after the blocking part is opened, an even more sufficient flow path of the blood from the first blood drawing tube to the second blood drawing tube can be secured.

In the above-mentioned blood-bag system, the communicating part may be disposed on a side of the second port with respect to the blocking part in the tube-shaped body. With this configuration, before the blocking part is opened by the communicating part, blood introduced from the first port is introduced as it is to a hollow section of the branching tube and the third port, and hence a sufficient flow path of the blood can be secured.

In the above-mentioned blood-bag system, the bag may include a blood drawing bag for accommodating the blood drawn from a donor, and an initially-drawn blood bag for drawing initially-drawn blood in a blood drawing, and the tube may include a first blood drawing tube connected to a blood drawing needle to be punctured in the donor and connected to the first port that defines one end part of the body tube, a second blood drawing tube connected to the blood drawing bag and connected to the second port that defines a base end part positioned to the rear in the moving direction in the communicating part, and a branching tube connected to the initially-drawn blood bag and connected to the third port that defines one end part of the branching tube. With this configuration, before the blocking part is opened, an even more sufficient flow path of the blood from the first blood drawing tube to the branching tube can be secured.

According to the present invention, a flow path that branches in multiway can be switched with a simple operation, and a sufficient flow path of blood can be secured at the switching portion.

DESCRIPTION OF EMBODIMENTS

Figure 1:
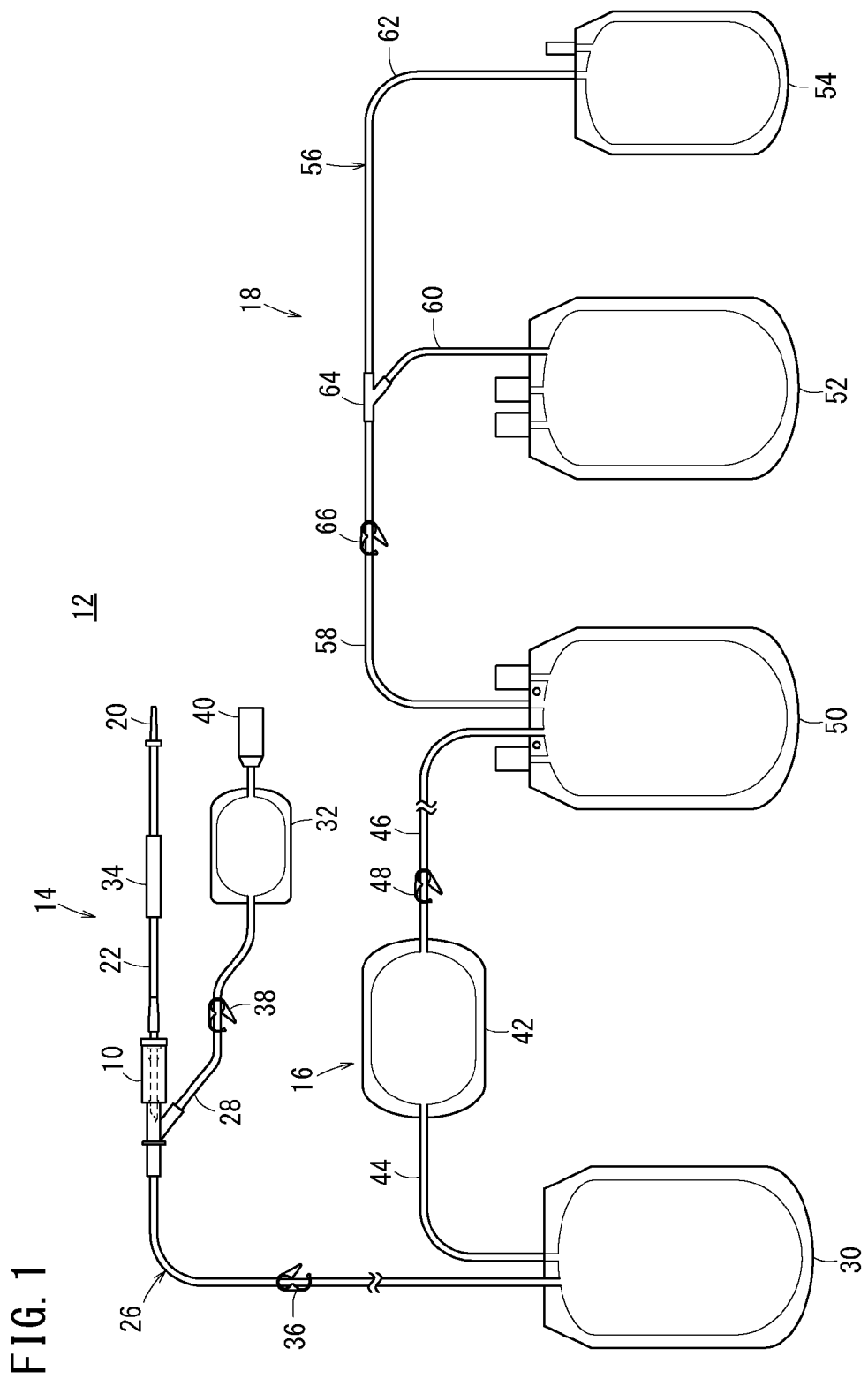
FIG. 1 is an overall configuration diagram of a blood-bag system including a blood-flow-path switching device according to an embodiment of the present invention.

Exemplary embodiments of a blood-flow-path switching device according to the present invention are explained in detail below with reference to the accompanying drawings. For the convenience of explanation, a ratio of dimensions of constituent elements in each of the drawings and a ratio of dimensions of the same constituent element in a plurality of drawings are appropriately changed, and hence the ratios in the drawings are not necessarily to match actual ratios.

FIG. 1 is an overall configuration diagram of a blood-bag system 12 including a blood-flow-path switching device 10 according to an embodiment of the present invention. The blood-bag system 12 separates blood that contains a plurality of components into a plurality of components different from one another, and accommodates and stores each of the components in a different bag.

The blood-bag system 12 includes a blood drawing apparatus 14 that draws blood (whole blood) from a subject (donor), a pre-processing part 16 that removes a predetermined blood component from the whole blood, and a separation processing part 18 that separates the residual blood components with the predetermined component removed into a plurality of blood components and accommodates each of the components in a different bag, and includes the blood-flow-path switching device 10 in the blood drawing apparatus 14.

The blood drawing apparatus 14 includes a blood drawing needle 20, a first blood drawing tube 22, a second blood drawing tube 26, a branching tube 28, a blood drawing bag 30, and an initially-drawn blood bag 32. The blood-flow-path switching device 10 is disposed, when branching the first blood drawing tube 22 into multiple tubes in the blood-bag system 12, at a branching portion, and in the present embodiment, specifically, connected to the first blood drawing tube 22, the second blood drawing tube 26, and the branching tube 28 in the blood drawing apparatus 14, and disposed to branch the first blood drawing tube 22 into the second blood drawing tube 26 and the branching tube 28.

The blood drawing needle 20 is punctured in the donor in order to draw the blood, connected to one end of the first blood drawing tube 22, and after use, protected by a needle cover 34 that is movable along the longitudinal direction of the first blood drawing tube 22.

The first blood drawing tube 22 is connected to one end of each of the second blood drawing tube 26 and the branching tube 28 via the blood-flow-path switching device 10, and the other ends of the second blood drawing tube 26 and the branching tube 28 are connected to the blood drawing bag 30 and the initially-drawn blood bag 32, respectively. Further, at halfway portions of the second blood drawing tube 26 and the branching tube 28, clamps 36 and 38 for closing and opening flow paths of the second blood drawing tube 26 and the branching tube 28 are respectively provided.

The blood drawing bag 30 is a bag for accommodating the blood (whole blood) drawn from the donor. The blood drawing bag 30 is connected to the pre-processing part 16 via an inlet side tube 44.

The initially-drawn blood bag 32 is connected to a sampling port 40, and by mounting a blood drawing tube (not shown) to the sampling port 40, the initially drawn blood is collected. The collected initially-drawn blood is used as test blood.

Each of the blood drawing bag 30 and the initially-drawn blood bag 32 is configured in a pouched shape by laminating soft resin sheet members having flexibility, such as polyvinyl chloride or polyolefin and fusing or bonding an edge portion.

When drawing the blood from the donor by using the blood drawing apparatus 14, before accommodating the blood in the blood drawing bag 30, firstly, a predetermined amount of the initial flow of the drawn blood is accommodated in the initially-drawn blood bag 32. In this case, by setting the clamp 38 to an open state while the blood-flow-path switching device 10 is in the initial state, i.e., a state before changing the flow path, the flow of the initially-drawn blood to a side of the second blood drawing tube 26, i.e., a side of the blood drawing bag 30 is prevented, and the initially-drawn blood is introduced to the initially-drawn blood bag 32 via the first blood drawing tube 22, the blood-flow-path switching device 10, and the branching tube 28.

Further, when accommodating the drawn blood in the blood drawing bag 30, by setting the blood-flow-path switching device 10 to a switched state, i.e., a state in which the flow path is switched, the clamp 36 to an open state, and the clamp 38 to a closed state, the drawn blood is introduced to the blood drawing bag 30 via the first blood drawing tube 22, the blood-flow-path switching device 10, and the second blood drawing tube 26. After introducing the blood to the blood drawing bag 30, the clamp 36 is set to a closed state.

The pre-processing part 16 includes a filter 42 that removes the predetermined blood component from the whole blood, the inlet side tube 44 with one end connected to the blood drawing bag 30 and the other end connected to an inlet of the filter 42, and an outlet side tube 46 with one end connected to an outlet of the filter 42 and the other end connected to the separation processing part 18.

The filter 42 is, for example, a white-blood-cell removing filter that removes a white blood cell as the predetermined blood component. Alternatively, the filter 42 can be a filter that removes a platelet.

The inlet side tube 44 is a tube for transferring the blood accommodated in the blood drawing bag 30 to the filter 42.

The outlet side tube 46 is a tube for transferring the residual blood components with the predetermined blood component removed by the filter 42 to the separation processing part 18. A clamp 48 for closing and opening a flow path of the outlet side tube 46 is provided at a halfway portion of the outlet side tube 46.

The separation processing part 18 includes a first bag 50 for accommodating the residual blood component with the predetermined blood component removed by the filter 42, a second bag 52 for accommodating a supernatent component such as a blood plasma obtained by separating the blood components in the first bag 50, a third bag 54 that accommodates a red-blood-cell preservative solution, and a transfer line 56 that is connected to the first, second, and third bags 50, 52, and 54.

In a similar manner to the blood drawing bag 30, each of the first, second, and third bags 50, 52, and 54 can be configured in a pouched shape with soft resin sheet members having flexibility.

The first bag 50 serves as both a bag for accommodating the residual blood components with the predetermined blood component removed by the filter 42 and a bag for storing a sedimentation component such as dense red blood cells obtained by separating the residual blood components. An MAP solution, an SAGM solution, an OPTISOL solution, or the like is used as the red-blood-cell preservative solution accommodated in the third bag 54.

The transfer line 56 includes a first transfer tube 58 connected to the first bag 50, a second transfer tube 60 connected to the second bag 52, a third transfer tube 62 connected to the third bag 54, a branching part 64 that connects the first, second, and third transfer tubes 58, 60, and 62, and a clamp 66 provided at a halfway portion of the first transfer tube 58 and configured to close and open a flow path of the first transfer tube 58.

Each of the tubes in the blood-bag system 12 is a transparent and flexible resin tube. Each of the clamps can be a standard product that is conventionally used, and at the time of sterilizing the blood-bag system 12 and at the time of storing the blood-bag system 12 before use, all the clamps at in an open state, and hence insides of the bags are communicated with one another to be in a uniform sterilized state.

The blood-flow-path switching device 10 according to the present embodiment is explained below.

Figure 2:
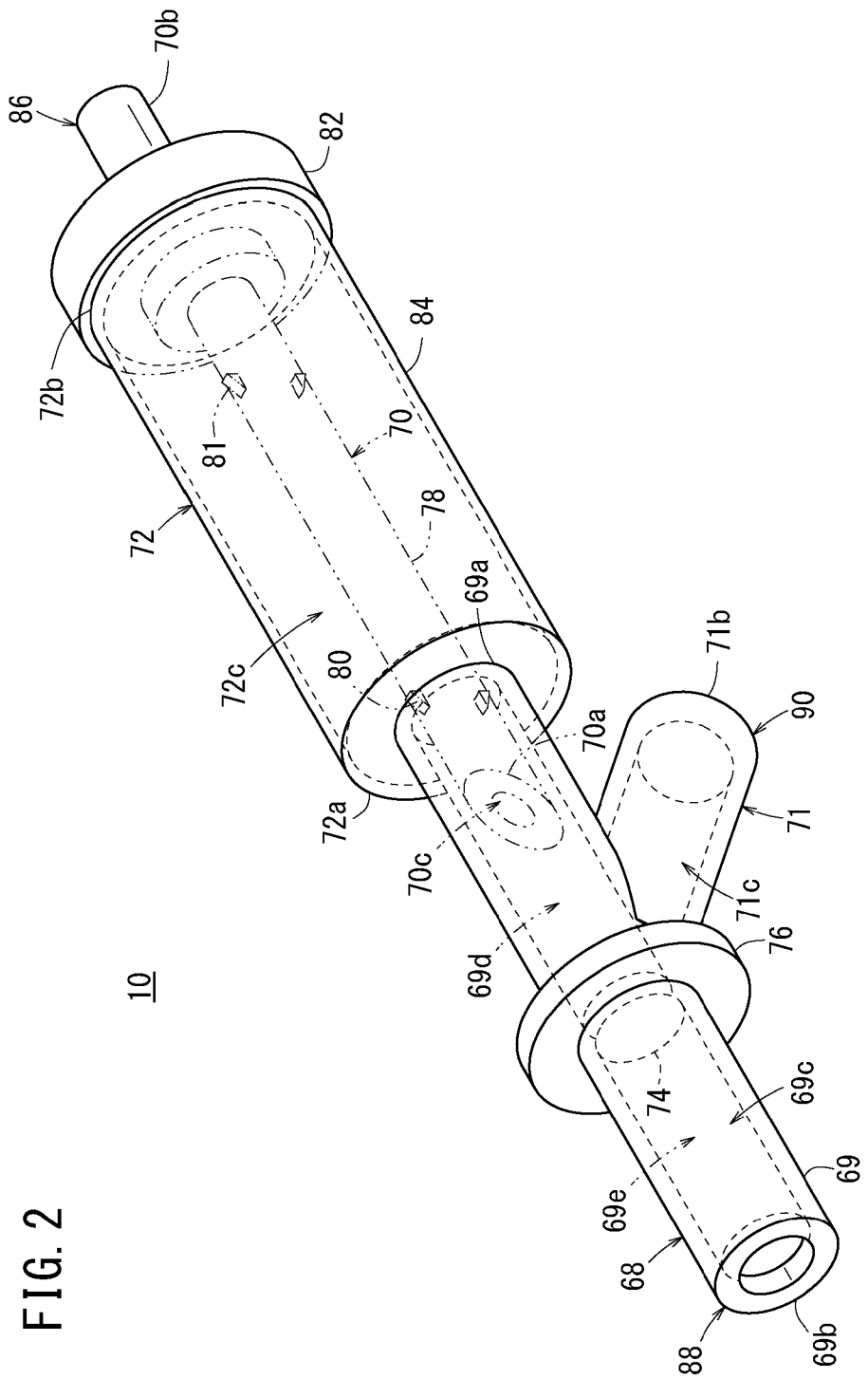
FIG. 2 is a perspective view of the blood-flow-path switching device shown in FIG. 1.

FIG. 2 is a perspective view of the blood-flow-path switching device 10 according to the present embodiment. The blood-flow-path switching device 10 includes a tube-shaped body 68 including a blocking part 74, a communicating part 70 that opens the blocking part 74, and a cover part 72 that covers the communicating part 70.

The blood-flow-path switching device 10 further includes at least a first port 86, a second port 88 that define an inlet and an outlet of a fluid such as blood, respectively, and a third port 90. In the blood-flow-path switching device 10, the first port 86 is disposed on one side with respect to the blocking part 74, the second port 88 is disposed on the other side with respect to the blocking part 74, and the third port 90 is disposed on a side of the first port 86 with respect to the blocking part 74. In an initial state before switching the flow path, i.e., a state before opening the blocking part 74, the communication of the first port 86 and the second port 88 is blocked by the blocking part 74, and the first port 86 and the third port 90 are communicated with each other.

The tube-shaped body 68 includes a branching tube 71 that is branched from a body tube 69 extending in an axial direction and extends in a direction branching from the axial direction. Each of the body tube 69 and the branching tube 71 is formed in a hollow shape, and hollow sections 69c and 71c of the body tube 69 and the branching tube 71 define flow paths of the blood. The body tube 69 and the branching tube 71 can be formed in an integrated manner.

A constituent material of the tube-shaped body 68 including the body tube 69 and the branching tube 71 is not limited in particular, and for example, a resin material can be used as the material. Further, the tube-shaped body 68 can be formed in a substantially transparent manner in order to secure a visibility inside the tube-shaped body 68.

Figure 3:
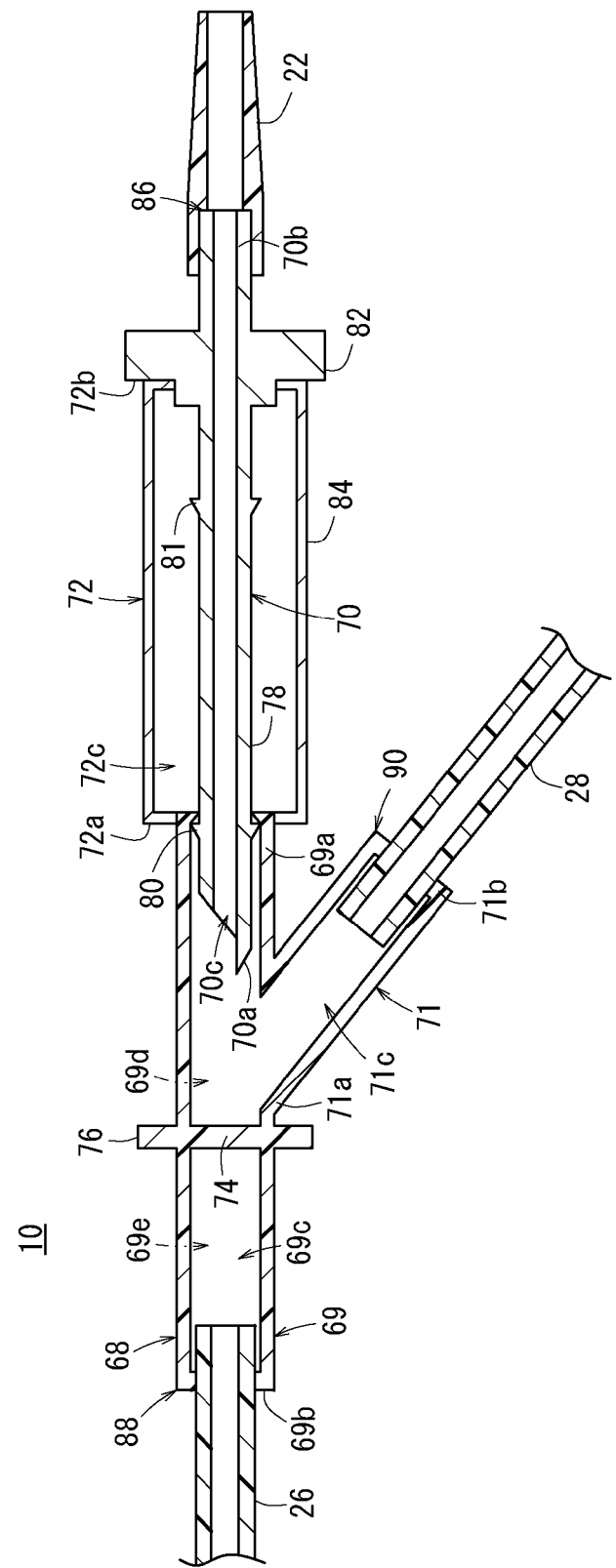
FIG. 3 is a lateral cross-sectional view of the blood-flow-path switching device shown in FIG. 1, showing a state before creating an opening on a blocking part.
Figure 4:
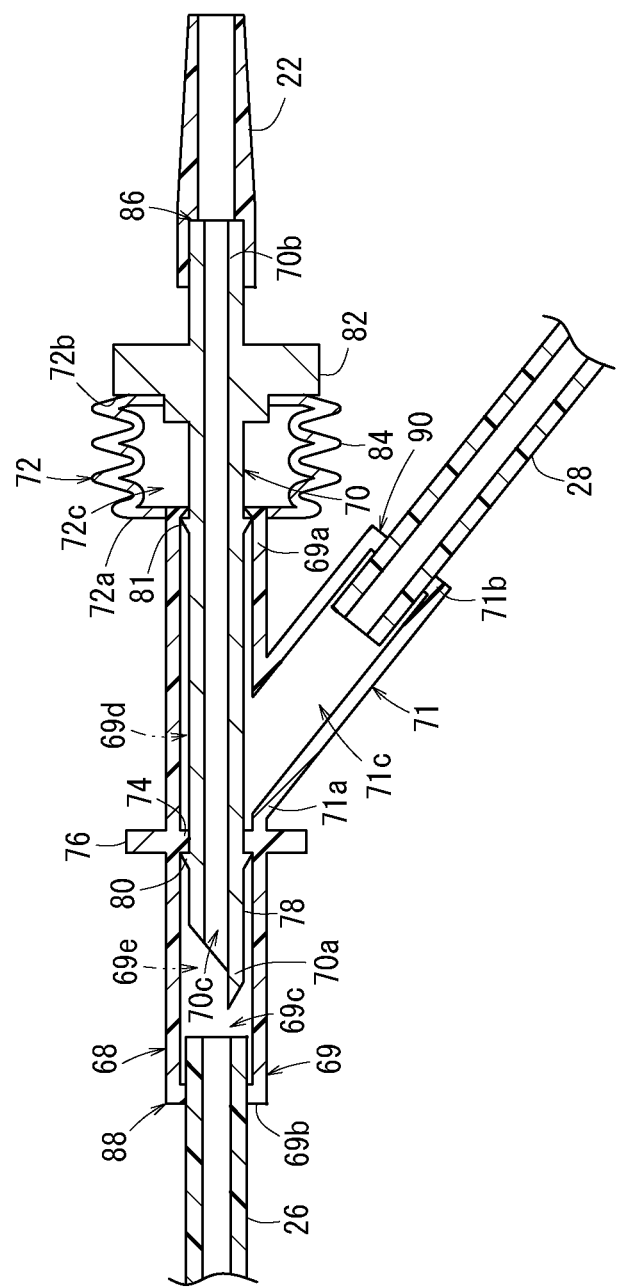
FIG. 4 is a lateral cross-sectional view of the blood-flow-path switching device shown in FIG. 1, showing a state after creating an opening on a blocking part.

The body tube 69 includes a first end part 69a that constitutes one end and a second end part 69b that constitutes the other end, and both the first end part 69a and the second end part 69b are opened with respect to the axial direction. The first end part 69a is connected to a distal end part 72a of the cover part 72. Further, the second end part 69b is configured to be connectable to a tube that defines a flow path of the blood, and for example, is connected to the second blood drawing tube 26. In the present embodiment, as shown in FIGS. 3 and 4, the second end part 69b of the body tube 69 is configured as the second port 88.

Further, the body tube 69 is configured in a manner that the communicating part 70 is slidable in the axial direction in the hollow section 69c, and an inner circumferential surface of the hollow section 69c has an internal diameter slightly larger than an outer diameter of the communicating part 70. The body tube 69 further includes the blocking part 74 that blocks the flow path at a halfway portion of the hollow section 69c. That is, in the hollow section 69c, a first hollow section 69d on a side of the first end part 69a with respect to the blocking part 74 and a second hollow section 69e on a side of the second end part 69b with respect to the blocking part 74 are blocked by the blocking part 74.

In the body tube 69, a flow path through the second port 88 is in a closed state by the blocking part 74 before being opened blocking the first hollow section 69d and the second hollow section 69e, but in an open state by a hollow section 70c of the communicating part 70 that opens the blocking part 74 being communicated with the second hollow section 69e.

The branching tube 71 is connected to the halfway portion of the body tube 69, and for example, is connected on the side of the first port 86 with respect to the blocking part 74.

Both a first end part 71a and a second end part 71b of the branching tube 71 are opened, and the hollow section 71c of the branching tube 71 is communicated with the hollow section 69d of the body tube 69. For example, the first end part 71a of the branching tube 71 is connected on a side of the first end part 69a with respect to the blocking part 74 on an outer circumferential surface of the body tube 69, and an opening portion of the branching tube 71 is communicated with the first hollow section 69d of the body tube 69. On the other hand, the second end part 71b of the branching tube 71 is configured to be connectable to a tube that defines a flow path of the blood, and for example, is connected to the branching tube 28. In the present embodiment, as shown in FIGS. 3 and 4, the second end part 71b of the branching tube 71 is configured as the third port 90. The branching tube 71 can be formed with an inner diameter of the hollow section 71c equivalent to that of the hollow section 69c of the body tube 69.

In the branching tube 71, a flow path through the third port 90 is opened or closed by a movement of the communicating part 70 in the hollow section 69c of the body tube 69, and for example, when the communicating part 70 makes no movement in the initial state, the hollow section 70c of the communicating part 70 and the hollow section 71c of the branching tube 71 are communicated with each other to be in an open state. On the other hand, when the communicating part 70 moves so that the first end part 71a is blocked by an outer circumferential surface of the communicating part 70 or the like, the communication of the hollow section 70c of the communicating part 70 and the hollow section 71c of the branching tube 71 is blocked to be in a closed state.

That is, in the tube-shaped body 68, the flow path through the second port 88 and the flow path through the third port 90 are switched according to the movement of the communicating part 70 in the hollow section 69c of the body tube 69.

The tube-shaped body 68 can be formed to include a flange part 76 that protrudes in an outward direction on an outer circumference of the tube-shaped body 68, such that an operator can easily operate the blood-flow-path switching device 10 by putting a finger on the flange part 76. The flange part 76 can be disposed at the same position as the blocking part 74 in the axial direction of the tube-shaped body 68, or can be disposed at a different position.

The blocking part 74 closes the flow path in a liquid-tight manner at the halfway portion of the hollow section 69c of the body tube 69, and for example, is formed to have a film or a partition for partitioning the flow path in front or back of the blocking part 74. The blocking part 74 is configured to be opened according to the movement of the communicating part 70 with respect to the tube-shaped body 68.

The blocking part 74 according to the present embodiment is integrated with the body tube 69 at the halfway portion of the hollow section 69c of the body tube 69, i.e., provided in an integrated manner with the tube-shaped body 68, and is penetrated and opened by the communicating part 70 that moves with respect to the tube-shaped body 68. When the blocking part 74 is penetrated by the communicating part 70, the hollow section 70c of the communicating part 70 and the second hollow section 69e of the body tube 69 become communicated with each other, by which the flow path through the second port 88 becomes in an open state.

A constituent material of the blocking part 74 is not limited in particular as long as it can be penetrated by the communicating part 70, that is a material softer than the communicating part 70, and for example, an elastic material or a soft resin material can be used as the material.

The communicating part 70 is configured to be movable in the axial direction in the hollow section 69c of the body tube 69, and has an outer diameter slightly smaller than the inner diameter of the hollow section 69c. The communicating part 70 is movable to a predetermined moving position toward the blocking part 74 in the hollow section 69c, and hereinafter, a direction in which the communicating part 70 is headed for the blocking part 74 is referred to as a moving direction of the communicating part 70.

The communicating part 70 is formed in a hollow shape with an opening in the axial direction, the hollow section 70c of the communicating part 70 defines the flow path of the blood, the communicating part 70 includes a distal end part 70a positioned to the front in the moving direction in the communicating part 70 and a base end part 70b positioned to the rear in the moving direction, and both the distal end part 70a and the base end part 70b are opened with respect to the axial direction.

As shown in FIGS. 3 and 4, for example, the communicating part 70 is disposed on the side of the first port 86 with respect to the blocking part 74 in the tube-shaped body 68, i.e., the side of the first end part 69a of the body tube 69, and is inserted into the hollow section 69c of the body tube 69 from the side of the first end part 69a. That is, the direction headed for the side of the second end part 69b from the side of the first end part 69a of the body tube 69 is the moving direction of the communicating part 70.

When the communicating part 70 moves in the moving direction with respect to the tube-shaped body 68, the communicating part 70 acts against the blocking part 74, for example, by penetrating the blocking part 74, the communicating part 70 can open the blocking part 74.

The communicating part 70 can penetrate the blocking part 74 in the tube-shaped body 68, and includes a body part 78 that penetrates the blocking part 74 on a side of the distal end part 70a. The distal end part 70a of the communicating part 70 is a distal end part of the body part 78, and the distal end part has a shape that is suitable for penetrating the blocking part 74, which for example, can be formed in a sharp needle end shape. Further, the base end part 70b of the communicating part 70 is configured to be connectable to a tube that defines a flow path of the blood, and for example, is connected to the first blood drawing tube 22. In the present embodiment, as shown in FIGS. 3 and 4, the base end part 70b of the communicating part 70 is configured as the first port 86.

When the communicating part 70 moves to the predetermined moving position in the moving direction with respect to the tube-shaped body 68, the body part 78 blocks the first end part 71a of the branching tube 71, by which the communication of the hollow section 70c of the communicating part 70 and the hollow section 71c of the branching tube 71 is blocked, i.e., the flow path through the third port 90 is closed. The body part 78 has a length that is sufficient to penetrate the blocking part 74, i.e., a length and an outer circumferential surface that are sufficient to block the branching tube 71 at the time of penetrating the blocking part 74.

A constituent material of the communicating part 70 is not limited in particular so long as is can penetrate the blocking part 74, i.e., a material harder than the blocking part 74, and for example, a hard resin material can be used as the material. Further, the communicating part 70 can be formed in a substantially transparent manner in order to secure a visibility inside the communicating part 70.

Further, the communicating part 70 includes support parts 80 and 81 that support the communicating part 70 with respect to the tube-shaped body 68 and the cover part 72 on an outer circumference of the communicating part 70. Each of the support parts 80 and 81 can be a simple protrusion that protrudes in an outward direction at a predetermined position on the outer circumference of the communicating part 70 or a tapered ring-shaped part that protrudes in the outward direction formed in a manner that an outer diameter increases toward the side of the base end part 70b extending in the circumferential direction on the outer circumference of the communicating part 70.

The support part 80 provided on the side of the distal end part 70a of the communicating part 70 is configured to be engaged with the tube-shaped body 68 in the initial state before the blocking part 74 is opened, and in a switched state after the blocking part 74 is opened, to be engaged with the blocking part 74. Further, the support part 81 provided on the side of the base end part 70b of the communicating part 70 is configured to be engaged with the tube-shaped body 68 in the switched state after the blocking part 74 is opened.

In this manner, the support part 80 temporarily prevents the movement of the communicating part 70 in the axial direction with respect to the tube-shaped body 68 in the initial state before the blocking part 74 is opened. Further, in the switched state after the blocking part 74 is opened, the support parts 80 and 81 respectively prevent the movement of the communicating part 70 in the axial direction with respect to the tube-shaped body 68 and the cover part 72. That is, the support parts 80 and 81 respectively act as retainers with respect to the tube-shaped body 68 and the cover part 72 of the communicating part 70.

The engagement of the support part 80 with respect to the tube-shaped body 68 has at least a strength that is enough to prevent the communicating part 70 from getting out of the tube-shaped body 68. Further, the engagement of the support part 80 with respect to the blocking part 74 has at least a strength that is enough to prevent the communicating part 70 from moving in a direction opposite to the moving direction with respect to the tube-shaped body 68 and enough to prevent the operator from easily pulling the communicating part 70 out of the tube-shaped body 68.

Further, the communicating part 70 includes a base part 82 that protrudes in the outward direction on the outer circumference of the communicating part 70, so that the communicating part 70 is configured in a manner that the operator can easily operate the blood-flow-path switching device 10 by putting a finger on the base part 82. The base part 82 can be provided between the body part 78 and the base end part 70b.

The cover part 72 can accommodate the communicating part 70 regardless of the movement of the communicating part 70 in the axial direction, and for example, is formed an a shrinkable manner according to the movement of the communicating part 70 in the moving direction.

The cover part 72 is formed in a hollow shape with an opening in the axial direction, which is in a pouched shape covering the communicating part 70 to accommodate the communicating part 70 in a hollow section 72c. For example, as shown in FIG. 2, the cover part 72 can be formed in a hollow tube shape with the same axial direction as the blood-flow-path switching device 10, or can be formed in an elliptical sphere shape, a sphere shape, or in an accordion shape.

Further, the cover part 72 includes the distal end part 72a positioned to the front in the moving direction in the communicating part 70, i.e., on the side of the distal end part 70a of the communicating part 70, and a base end part 72b positioned to the rear in the moving direction, i.e., on the side of the base end part 70b of the communicating part 70. The distal end part 72a is formed to have an opening portion into which the body part 78 of the communicating part 70 is insertable, which is connected to the tube-shaped body 68 in a liquid-tight manner. Further, the base end part 72b is connected to the communicating part 70 in a liquid-tight manner, and for example, is connected on the side of the base end part 70b such as the base part 82 in the communicating part 70, and is movable in the axial direction together with the communicating part 70. With this configuration, the cover part 72 enables the communicating part 70 to be kept clean, and prevents the fluid from leaking outside even if the fluid leaks from the communicating part 70.

As shown in FIGS. 3 and 4, for example, the cover part 72 is disposed on the side of the first end part 69a of the body tube 69 in the tube-shaped body 68, and the distal end part 72a of the cover part 72 is connected to the first end part 69a of the body tube 69.

An outer circumferential portion of the cover part 72, i.e., a body part 84 except for the distal end part 72a and the base end part 72b of the cover part 72 can be formed in a shrinkable manner in the axial direction.

A constituent material of the cover part 72 is not limited in particular so long as it is a soft material that is shrinkable with respect to the axial direction, and for example, an elastic material or a soft resin material can be used as the material. The cover part 72 can be formed in a substantially transparent manner in order to secure a visibility inside the cover part 72.

The blood-flow-path switching device 10 according to the embodiment of the present invention is basically configured in the above manner, and its operation and effect are described below with a case of switching a blood flow path using the blood-flow-path switching device 10 as an example.

Firstly, as shown in FIG. 3, in the blood-flow-path switching device 10, the first hollow section 69d and the second hollow section 69e of the body tube 69 are blocked by the blocking part 74 in an initial state, i.e., a state before the blocking part 74 is opened. Therefore, a communication of the hollow section 70c of the communicating part 70 and the second hollow section 69e of the body tube 69 is blocked, and at the same time, a communication of the first port 86 and the second port 88 is blocked, i.e., the flow path through the second port 88 is closed. On the other hand, the hollow section 70c of the communicating part 70 and the hollow section 71c of the branching tube 71 are communicated with each other, and at the same time, the first port 86 and the third port 90 are communicated with each other, i.e., the flow path through the third port 90 is opened.

With this configuration, in the blood-bag system 12, a flow of the blood from the first blood drawing tube 22 to the second blood drawing tube 26 is blocked, and a flow of the blood from the first blood drawing tube 22 to the branching tube 28 is allowed.

At this moment, the clamp 38 is opened at the branching tube 28, and the initially-drawn blood drawn from the donor is introduced to the initially-drawn blood bag 32 via the first blood drawing tube 22, the blood-flow-path switching device 10, and the branching tube 28.

Further, in the blood-flow-path switching device 10, the support part 80 of the communicating part 70 is engaged with the tube-shaped body 68, and hence the communicating part 70 is prevented from getting out of the cover part 72 and the tube-shaped body 68.

The operator then pushes the communicating part 70 in the moving direction against the tube-shaped body 68 in order to introduce the blood drawn from the donor to the blood drawing bag 30, i.e., in order to allow the flow of the blood from the first blood drawing tube 22 to the second blood drawing tube 26.

At this moment, as shown in FIG. 4, the body part 84 of the cover part 72 is shrunken in the axial direction, and a distance between the distal end part 72a and the base end part 72b of the cover part 72 is shortened.

The body part 78 of the communicating part 70 moves in the moving direction in the hollow section 69c of the body tube 69 in the tube-shaped body 68, abuts and penetrates the blocking part 74, and the communicating part 70 finally moves to the predetermined moving position. With this operation, the blocking part 74 is opened, and the distal end part 70a of the communicating part 70 is positioned on the side of the second hollow section 69e of the body tube 69 with respect to the blocking part 74 in the tube-shaped body 68, and hence the hollow section 70c of the communicating part 70 and the second hollow section 69e of the body tube 69 are communicated with each other, and at the same time, the first port 86 and the second port 88 are communicated with each other, i.e., the flow path through the second port 88 is opened.

Further, the communicating part 70 that has moved to the predetermined moving position blocks the first end part 71a of the branching tube 71 in the tube-shaped body 68, and with this operation, the communication of the hollow section 70c of the communicating part 70 and the hollow section 71c of the branching tube 71 is blocked, and at the same time, the communication of the first port 86 and the third port 90 is blocked, i.e., the flow path through the third port 90 is closed.

Moreover, in the communicating part 70, at least one of the engagement of the support part 80 on the side of the distal end part 70a with the blocking part 74 or the engagement of the support part 81 on the side of the base end part 70b with the tube-shaped body 68 is performed, and hence the communicating part 70 is supported with respect to the tube-shaped body 68 while maintaining a communicated state of the hollow section 70c of the communicating part 70 and the second hollow section 69e of the body tube 69.

In this manner, in the blood-bag system 12, the flow of the blood from the first blood drawing tube 22 to the branching tube 28 is blocked, and the first blood drawing tube 22 and the second blood drawing tube 26 are communicated with each other, so that the flow of the blood from the first blood drawing tube 22 to the second blood drawing tube 26 is allowed.

In this manner, in the present embodiment, the blood-flow-path switching device 10 can switch the flow path connected to the blood-flow-path switching device 10 by simply pushing the communicating part 70 in a push-in direction with respect to the tube-shaped body 68, and in this switching operation, the hollow section 70c of the communicating part 70 and the first hollow section 69d of the body tube 69 in the tube-shaped body 68 are communicated with each other, and hence the blood can smoothly flow through the flow path. Therefore, the flow path that is branched in multiway can be switched by an easy operation, and at the same time, a sufficient flow path of the blood can be secured at the switching portion.

Further, in the blood-flow-path switching device 10 according to the present invention, it can be configured such that, when the blocking part 74 in the tube-shaped body 68 is penetrated by the communicating part 70, the broken portion works as a seal for sealing off a space between the inner circumferential surface of the body tube 69 and the outer circumferential surface of the communicating part 70. With this sealing, when the blocking part 74 is penetrated, the communication of the hollow section 70c of the communicating part 70 and the hollow section 71c of the branching tube 71 is blocked for sure, and at the same time, the communication of the first port 86 and the third port 90 can be blocked for sure.

Moreover, the blood-flow-path switching device 10 according to the present invention can be configured such that by providing a ring-shaped seal part (not shown) on the inner circumferential surface near the blocking part 74 in the body tube 69 of the tube-shaped body 68, when the blocking part 74 is penetrated by the communicating part 70, the seal part seals off the space between the inner circumferential surface of the body tube 69 and the outer circumferential surface of the communicating part 70. With this sealing, when the blocking part 74 is penetrated, the communication of the hollow section 70c of the communicating part 70 and the hollow section 71c of the branching tube 71 can be blocked more securely, and at the same time, the communication of the first port 86 and the third port 90 can be blocked more securely.

In the above-mentioned embodiment, the blood-flow-path switching device 10 is applied to the blood-bag system 12 having a configuration in which the blood drawing apparatus 14 and the separation processing part 18 are connected to each other in an integrated manner from the beginning; however, the blood-flow-path switching device 10 can also be applied to a blood-component drawing system of a type in which a part (blood drawing system) corresponding to the blood drawing apparatus 14 and a part (separating system) corresponding to the separation processing part 18 are separated from each other. In such a blood-component drawing system, the whole blood is drawn by the blood drawing system, then a blood drawing bag (whole-blood bag) in the blood drawing system and the separating system are connected to each other, and blood components such as the platelet and the red blood cell are separated and drawn from the whole blood in the blood drawing bag. The blood-flow-path switching device 10 can be disposed on a tube that forms a flow path of the blood in such a blood drawing system or separating system.

Further, the blood-flow-path switching device 10 according to the present invention can be applied to a medical instrument including a flow path of a fluid other than the blood and disposed on the flow path.

Moreover, in the above-mentioned embodiment, the blood-flow-path switching device 10 connects the base end part 70b of the communicating part 70 on an upstream side with respect to the flow of the blood and connects the second end part 69b of the body tube 69 to a blood flow path on a downstream side; however, the second end part 69b of the body tube 69 can be connected to a blood flow path on the upstream side, and the base end part 70b of the communicating part 70 can be connected to a blood flow path on the downstream side.

Figure 5:
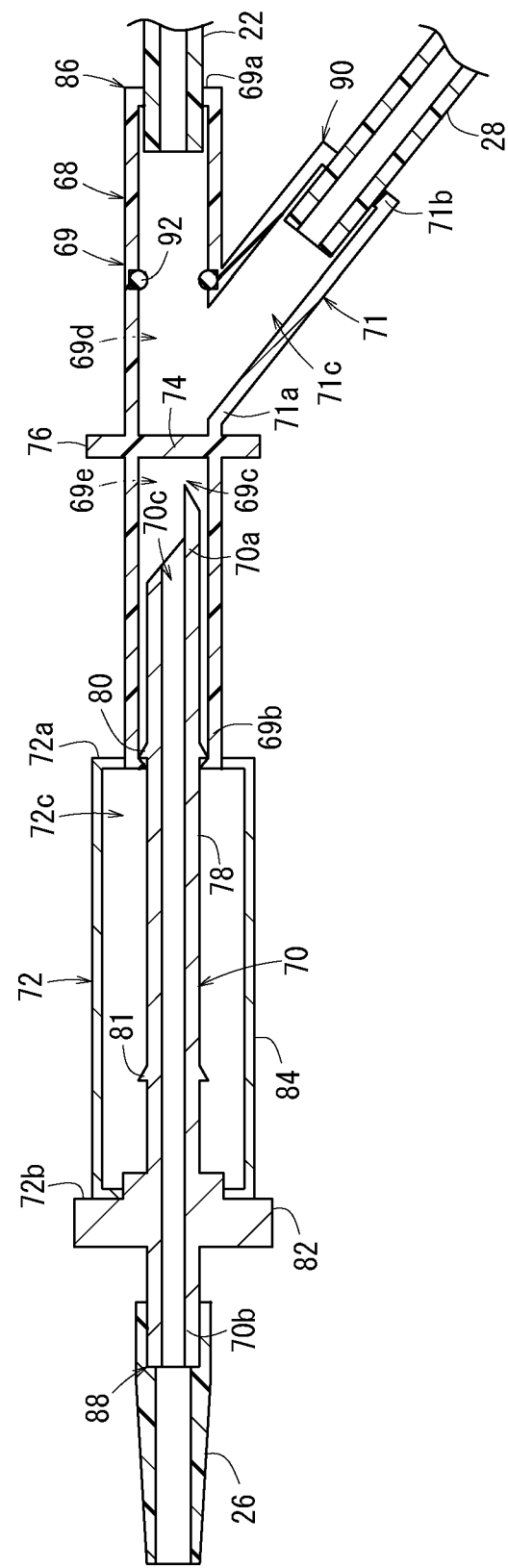
FIG. 5 is a lateral cross-sectional view of a modification example of the blood-flow-path switching device shown in FIG. 1, showing a state before creating an opening on a blocking part.
Figure 6:
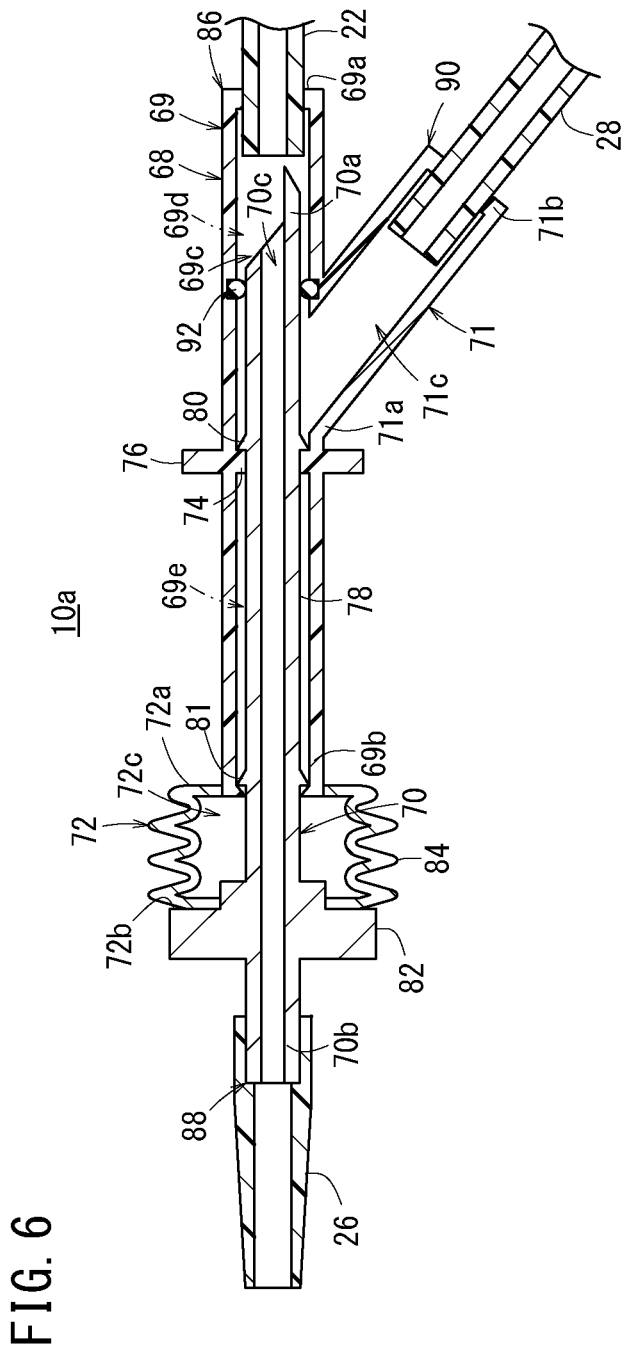
FIG. 6 is a lateral cross-sectional view of the modification example of the blood-flow-path switching device shown in FIG. 1, showing a state after creating an opening on a blocking part.

As shown in FIGS. 1 to 4, the blood-flow-path switching device 10 can be configured such that the communicating part 70 is disposed on the side of the first port 86 with respect to the blocking part 74 in the tube-shaped body 68, i.e., the side of the first end part 69a of the body tube 69, and the direction from the side of the first end part 69a of the body tube 69 toward the side of the second end part 69b is defined as the moving direction of the communicating part 70; however, for example, as a blood-flow-path switching device 10a according to a modification example shown in FIGS. 5 and 6, it can be configured such that the communicating part 70 is disposed on the side of the second port 88 with respect to the blocking part 74 in the tube-shaped body 68, i.e., the side of the second end part 69b of the body tube 69, and the direction from the side of the second end part 69b of the body tube 69 toward the side of the first end part 69a is defined as the moving direction of the communicating part 70. In FIGS. 5 and 6, the same reference sign as that shown in FIGS. 1 to 4 indicates the same or similar configuration.

In the blood-flow-path switching device 10a according to the modification example, the communicating part 70 is disposed on the side of the second end part 69b of the body tube 69, and hence as shown in FIG. 5, in an initial state, i.e., a state before the blocking part 74 is opened, the first hollow section 69d of the body tube 69 and the hollow section 71c of the branching tube 71 are communicated with each other, and at the same time, the first port 86 and the third port 90 are communicated with each other, i.e., the flow path through the third port 90 is opened. Further, in a similar manner to the above-described example, the communication of the hollow section 70c of the communicating part 70 and the first hollow section 69d of the body tube 69 is blocked, and at the same time, the communication of the first port 86 and the second port 88 is blocked, i.e., the flow path through the second port 88 is closed.

With this configuration, in the blood-bag system 12, the flow of the blood from the first blood drawing tube 22 to the second blood drawing tube 26 is blocked, and the flow of the blood from the first blood drawing tube 22 to the branching tube 28 is allowed.

Further, as shown in FIG. 6, when the communicating part 70 is pushed in the moving direction against the tube-shaped body 68, so that the body part 78 of the communicating part 70 abuts and penetrates the blocking part 74, and the communicating part 70 moves to the predetermined moving position, the blocking part 74 is opened, the distal end part 70a of the communicating part 70 is positioned on the side of the first hollow section 69d with respect to the blocking part 74 in the tube-shaped body 68, the hollow section 70c of the communicating part 70 and the first hollow section 69d of the body tube 69 are communicated with each other, and at the same time, the first port 86 and the second port 88 are communicated with each other, i.e., the flow path through the second port 88 is opened.

Moreover, the communicating part 70 that has moved to the predetermined moving position blocks the first end part 71a of the branching tube 71 in the tube-shaped body 68, and with this operation, the communication of the first hollow section 69d of the body tube 69 and the hollow section 71c of the branching tube 71 is blocked, and at the same time, the communication of the first port 86 and the third port 90 is blocked, i.e., the flow path through the third port 90 is closed.

Further, in the communicating part 70, at least one of the engagement of the support part 80 on the side of the distal end part 70a with the blocking part 74 or the engagement of the support part 81 on the side of the base end part 70b with the tube-shaped body 68 is performed, and hence the communicating part 70 is supported with respect to the tube-shaped body 68 while maintaining a communicated state of the hollow section 70c of the communicating part 70 and the first hollow section 69d of the body tube 69.

In this manner, in the blood-bag system 12, the flow of the blood from the first blood drawing tube 22 to the branching tube 28 is blocked, and the first blood drawing tube 22 and the second blood drawing tube 26 are communicated with each other, so that the flow of the blood from the first blood drawing tube 22 to the second blood drawing tube 26 is allowed.

In this manner, the blood-flow-path switching device 10a according to the modification example has substantially the same operation and effect as those of the blood-flow-path switching device 10 in which the communicating part 70 is disposed on the side of the first end part 69a of the body tube 69 as described above; however, because the blood introduced from the first port 86 is introduced to the third port 90 via the first hollow section 69d of the body tube 69 and the hollow section 71c of the branching tube 71 without passing the hollow section 70c of the communicating part 70 in the initial state before the blocking part 74 is opened, compared to the above-mentioned blood-flow-path switching device 10, blood-flow-path switching device 10a has a configuration that can secure an even more sufficient flow path of the blood in the initial state, and hence the flow of the blood from the first blood drawing tube 22 to the branching tube 28 becomes more smooth in the blood-bag system 12.

Further, the blood-flow-path switching device 10a according to the modification example can be configured such that a ring-shaped seal part 92 is provided on the inner circumferential surface on the side of the first end part 69a with respect to the branching tube 71 in the first hollow section 69d of the body tube 69, and when the communicating part 70 penetrates the blocking part 74 and moves to the predetermined moving position, the seal part 92 seal off the space between the inner circumferential surface of the body tube 69 and the outer circumferential surface of the communicating part 70. With this sealing, the communication of the first hollow section 69d of the body tube 69 and the hollow section 71c of the branching tube 71 is blocked for sure, and at the same time, the communication of the first port 86 and the third port 90 can be blocked for sure.

In addition, it goes without saying that the blood-flow-path switching device according to the present invention is not limited to the above-mentioned embodiments, but various modifications may be made without departing from the gist of the present invention.

The invention claimed is:

1. A blood-flow-path switching device, comprising a tube-shaped body and a communicating part each having a flow path of a fluid in a hollow section formed in a hollow shape, wherein the tube-shaped body includes
    a body tube in a hollow shape extending in an axial direction, and
    a branching tube in a hollow shape connected to a halfway portion of the body tube (69) extending in a direction branching from the axial direction,
    the hollow section of the body tube includes a blocking part for blocking a flow of the fluid in the hollow section,
    the blocking part blocks a communication of a first port disposed on one side with respect to the blocking part and a second port disposed on the other side,
    the branching tube is connected to the body tube on a side of the first port with respect to the blocking part and includes a third port (90) disposed on the side of the first port (86) with respect to the blocking part and communicable with the first port,
    the communicating part is movable in the axial direction in the hollow section of the body tube (69) and is disposed in a movable manner to a predetermined moving position in a moving direction toward the blocking part, and
    when the communicating part moves to the predetermined moving position, the communication of the first port and the third port is blocked, the blocking part is opened, and the first port and the second port are communicated with each other.

2. The blood-flow-path switching device according to claim 1, further comprising a cover part in a hollow shape shrinkable in the axial direction and configured to accommodate the communicating part, wherein
    a distal end part positioned to the front in the moving direction in the cover part is connected to the body tube in a liquid-tight manner, and
    a base end part positioned to the rear in the moving direction in the cover part (72) is connected to the communicating part in a liquid-tight manner and provided to be movable in the axial direction together with the communicating part.

3. The blood-flow-path switching device according to claim 2, wherein the cover part is formed in an accordion shape.

4. The blood-flow-path switching device according to claim 1, wherein the communicating part is disposed on the side of the first port with respect to the blocking part in the tube-shaped body.

5. The blood-flow-path switching device according to claim 1, wherein the communicating part is disposed on a side of the second port with respect to the blocking part in the tube-shaped body.

6. The blood-flow-path switching device according to claim 1, wherein the hollow section defines the flow path of the communicating part,
a distal end part positioned to the front in the moving direction in the communicating part constitutes the communicating part on a side of the blocking part and is formed in a shape capable of penetrating the blocking part, and
the blocking part is opened by being penetrated by the communicating part that moves in the moving direction with respect to the body tube.

7. A blood-bag system, comprising:
a bag for accommodating blood or blood component;
a tube that defines a flow path of the blood or the blood component to the bag; and
a blood-flow-path switching device disposed for the tube, wherein
the blood-flow-path switching device includes a tube-shaped body and a communicating part each having a flow path of a fluid in a hollow section formed in a hollow shape,
the tube-shaped body includes
a body tube in a hollow shape extending in an axial direction, and
a branching tube in a hollow shape connected to a halfway portion of the body tube and extending in a direction branching from the axial direction,
the hollow section of the body tube includes a blocking part for blocking a flow of the fluid in the hollow section,
the blocking part blocks a communication of a first port disposed on one side with respect to the blocking part and a second port disposed on the other side,
the branching tube is connected to the body tube on a side of the first port with respect to the blocking part and includes a third port disposed on the side of the first port with respect to the blocking part and communicable with the first port,
the communicating part is movable in the axial direction in the hollow section of the body tube and is disposed in a movable manner to a predetermined moving position in a moving direction toward the blocking part, and
when the communicating part moves to the predetermined moving position, the communication of the first port and the third port is blocked, the blocking part is opened, and the first port and the second port are communicated with each other.

8. The blood-bag system according to claim 7, wherein the blood-flow-path switching device further includes a cover part in a hollow shape shrinkable in the axial direction and configured to accommodate the communicating part,
a distal end part positioned to the front in the moving direction in the cover part is connected to the body tube in a liquid-tight manner, and
a base end part positioned to the rear in the moving direction in the cover part is connected to the communicating part in a liquid-tight manner, and provided to be movable in the axial direction together with the communicating part.

9. The blood-bag system according to claim 8, wherein the communicating part is disposed on a side of the second port with respect to the blocking part in the tube-shaped body.

10. The blood-bag system according to claim 9, wherein the bag includes
a blood drawing bag for accommodating the blood drawn from a donor, and
an initially-drawn blood bag for drawing initially-drawn blood in a blood drawing, and
the tube includes
a first blood drawing tube connected to a blood drawing needle to be punctured in the donor and connected to the first port that defines one end part of the body tube,
a second blood drawing tube connected to the blood drawing bag and connected to the second port that defines a base end part positioned to the rear in the moving direction in the communicating part, and
a branching tube connected to the initially-drawn blood bag and connected to the third port that defines one end part of the branching tube.

11. The blood-bag system according to claim 9, wherein the bag includes
a blood drawing bag for accommodating the blood drawn from a donor, and
an initially-drawn blood bag for drawing initially-drawn blood in a blood drawing, and
the tube includes
a first blood drawing tube connected to a blood drawing needle to be punctured in the donor and connected to the first port that defines a base end part positioned to the rear in the moving direction in the communicating part,
a second blood drawing tube connected to the blood drawing bag and connected to the second port that defines one end part of the body tube, and
a branching tube connected to the initially-drawn blood bag and connected to the third port that defines one end part of the branching tube.

12. The blood-bag system according to claim 7, wherein the communicating part is disposed on the side of the first port with respect to the blocking part in the tube-shaped body.

* * * * *